United States Patent [19]

Chang et al.

[11] Patent Number: 4,654,449

[45] Date of Patent: Mar. 31, 1987

[54] FORMATION OF HALOGENATED HYDROCARBONS FROM HYDROCARBONS

[75] Inventors: Clarence D. Chang, Princeton; Patrick D. Perkins, Titusville, both of N.J.

[73] Assignee: Mobil Oil Corporation, New York, N.Y.

[21] Appl. No.: 448,112

[22] Filed: Dec. 9, 1982

[51] Int. Cl.[4] .............................................. C07C 17/24
[52] U.S. Cl. .................................................... 570/261
[58] Field of Search ........................ 570/261; 260/694

[56] References Cited

U.S. PATENT DOCUMENTS

| | | | |
|---|---|---|---|
| 2,956,084 | 10/1960 | Eng et al. | 570/197 |
| 2,979,541 | 4/1961 | Pitt et al. | 570/261 |
| 2,998,459 | 8/1961 | Baker et al. | 570/207 |
| 3,026,361 | 3/1962 | Pitt et al. | 570/261 |
| 3,254,023 | 5/1966 | Miale et al. | 570/247 |
| 3,499,941 | 3/1970 | Gwens et al. | 570/197 |
| 3,728,408 | 4/1973 | Tobias | 252/455 Z |
| 4,384,159 | 5/1983 | Diesen | 585/642 |

FOREIGN PATENT DOCUMENTS 2095244  9/1982  United Kingdom ................ 570/254

*Primary Examiner*—Natalie Trousof
*Assistant Examiner*—Joseph A. Boska
*Attorney, Agent, or Firm*—A. J. McKillop; M. G. Gilman; M. V. Schneller

[57] ABSTRACT

Hydrocarbons and other compounds are halogenated to halocarbon products by contact with a halocarbon in the presence of an acidic zeolite catalyst such as ZSM-5. The process is particularly useful for the halogenation of methane to form chemicals of higher value.

25 Claims, No Drawings

FORMATION OF HALOGENATED HYDROCARBONS FROM HYDROCARBONS

FIELD OF THE INVENTION

This invention relates to a process for producing halogenated hydrocarbons (halocarbons) from hydrocarbons, especially methane.

BACKGROUND OF THE INVENTION

Halogenated hydrocarbons, which may also be referred to as halocarbons, are important industrial chemicals and are produced in large quantities for various purposes. The chlorocarbons are collectively the most important halocarbons in industry and commerce but other halocarbons, especially the fluorohalocarbon refrigerants widely sold under "Freon" trademark are also important products. Examples of common halocarbons include methyl chloride, methylene chloride, chloroform, carbon tetrachloride, methyl bromide, methyl iodide, ethyl chloride, the dichloroethanes: 1,1-dichloroethane (ethylidene dichloride) and 1,2-dichloroethane (dichloroethylene), trichloroethylene, tetrachloroethylene, allyl chloride. These and other chlorocarbons are described in Kirk-Othmer, Encyclopedia of Chemical Technology, Third Edition, John Wiley & Sons, New York 1979, Vol. 5, 668–848, to which reference is made for details of these materials, their preparation and their uses. The brominated hydrocarbons, fluorinated hydrocarbons and iodo-hydrocarbons are described respectively, in Kirk-Othmer, op cit, Vol. 4, 243–263; Vol. 10 829–925 and Vol. 11, 1–81; and Vol. 13, 667–671, to which reference is made for details of these compounds, their preparation and uses.

Halocarbons are produced by a variety of processes which vary according to the convenience, cost and availability of suitable starting materials. Methyl chloride, for example, may be made by the direct chlorination of methane or by the reaction of hydrogen chloride and methanol; the other chloromethanes may also be made by direct chlorination of methane, as described in Kirk-Othmer, op cit. The chloroethanes may be produced by the hydrochlorination of ethylene, dhlorination of ethane and other processes described in Kirk-Othmer, ibid. Other halocarbons may be produced by various processes, as described in Kirk-Othmer, ibid.

The preparative procedures which use the fully saturated hydrocarbons such as methane as a starting material normally require the halogen to be used in its most active form, e.g., chlorine, rather than in the form of a possibly more convenient and safe halogenating agent because the fully saturated hydrocarbons are less active than their unsaturated or substituted derivatives such as methanol or ethylene. The use of the halogen itself may, however, be undesirable because it is unselective in its reaction with the hydrocarbon, producing a range of halogenated products from the mono-substituted to the perhalo compound. It would therefore be desirable to find a way of improving the selectivity of the halogenation reaction as well as developing a halogenation procedure which is capable of halogenating the saturated hydrocarbons, especially methane, directly using convenient and safe halogenating agents.

SUMMARY OF THE INVENTION

It has now been found that halogenation reactions may be carried out using a halocarbon as the halogenating agent in the presence of a zeolite catalyst having acidic functionality. The reaction is of particular utility for the halogenation of hydrocarbons such as the straight chain alkanes, e.g. methane, but may also be employed with other halogen acceptors, e.g. other halocarbons. The reactant halocarbons used as the halogenating agent normally contain a plurality of halogen atoms in order to increase the yield of halocarbon product but since it is possible to obtain halocarbon products which are more highly halogenated than the reactant halocarbon, e.g. the products from reacting chloroform with methane over HZSM-5 include carbon tetrachloride, the reaction is not simply an equilibrium exchange between less and more highly halogenated species.

The present halogenation process is capable of producing halocarbons in good yields and in good selectivity, starting from hydrocarbon reactants such as methane. In this respect, it is notably superior to conventional hydrocarbon halogenation processes which employ the halogen itself as the halogenating agent and which produce a variety of halogenated products, thereby necessitating complicated and expensive separation procedures. The process may be used as a first step in the conversion of methane—a cheap and readily available commodity—to a wide variety of chemicals including vinyl chloride, ethylene, alkyl chloride, acetic acid, acetaldehyde, methanol, ethanol and styrene. Halomethanes produced by the process may also be used as alkylating agents in the production of high octane gasoline from naphtha and in the conversion of methane to BTX aromatics by the methylation of benzene with methyl chloride.

DETAILED DESCRIPTION

Reactants

The present process is capable of converting a wide range of compounds into the corresponding halocarbons. The process is primarily applicable to the halogenation of hydrocarbons, especially the alkanes, but other substrates (halogen acceptors) may also be used, for example, the halocarbons whose use is described below. Other substituted hydrocarbons may likewise be employed.

The process is of particular utility with saturated hydrocarbons, especially the alkanes, with a particular preference for the straight chain lower alkanes since these materials are capable of being readily sorbed by the zeolite, to permit the catalytic reaction to take place within the internal pore structure of the zeolite. In general, lower alkanes up to octane may be treated by the present process, although best results are obtained with the $C_4$ alkanes methane, ethane and propane, of which methane is preferred because of its availability at low cost from natural gas, the market for halomethanes and the readiness with methane enters into the reaction to produce halomethanes in good yield with high selectivity. However, the process may be used with other alkanes such as n-butane, iso-butane, tert-butane, n-pentane, the isomeric methyl butanes and n-hexane.

Aromatic hydrocarbons such as benzene, toluene or xylene will generally not be used because, if the reaction takes place at all, the nature of the products will be less predictable since the presence of halocarbons in the presence of aromatics and an acidic catalyst raises the possibility of Friedel-Crafts alkylation occurring, to give a number of more complex products whose identity will depend upon the pore size of the zeolite used. With zeolites of progressively larger pore size, products of greater molecular dimensions may be obtained since they will be able to obtain egress from the interior of the zeolite where they are formed. However, the reaction will be of greater complexity than the desired simple halogenation and for this reason, aromatic hydrocarbons will generally not be employed.

The hydrocarbon reactant is reacted with a halocarbon reactant which, for economic reasons, will normally be a chloro compound although if it is desired to produce products containing other halogens, bromo compounds, iodo compounds or fluoro compounds may also be employed. The invention will be described with particular reference to the use of chlorinated compounds, but similar considerations will apply to the use of compounds which contain bromine, iodine or fluorine as the halogen, although differences in reactivities may be noted, especially with the fluorocarbons.

The halocarbon reactant will normally be a polyhalocarbon, that is, a halocarbon which contains a number of halogen atoms in each molecule. The reason for this is first, that polyhalocarbon reactants can provide several halogens for more than one molecule of the hydrocarbon, e.g. one mole of chloroform is theoretically capable of chlorinating two moles of methane to form three moles of methyl chloride, and second, the selectivity to a single product is improved by decreasing the halogen content of a polyhalogen reactant and simultaneously increasing the halogen content of the hydrocarbon reactant so that the product contains the same halocarbons produced both by dehalogenation of the halocarbon reactant and by halogenation of the hydrocarbon, e.g. in the conversion of chloroform and methane to a single product such as methyl chloride. It is also preferred that the halocarbon reactant should have the same carbon skeleton as the hydrocarbon reactant, again, to improve the selectivity to the desired product; methane, therefore, should be halogenated with halomethanes, ethane with haloethanes and so forth. It should be remembered, of course, that since each carbon may be halogenated by up to four halogens in methane and by up to three halogens in other hydrocarbons, there is a possibility of introducing further and different halogens into a starting material which is itself halogenated. This provides a particular favorably synthetic route for mixed halocarbons such as the fluorohalocarbons, e.g. chlorodifluoromethane (Freon-22), chlorotrifluoromethane (Freon-13), dichlorodifluoromethane (Freon-22), dichlorofluoromethane (Freon-21) ("Freon" is a trademark), and the starting material may therefore itself be a halocarbon, preferably containing fewer halogens than the selected halocarbon halogenating agent.

Examples of suitable halocarbon reactants include methylene dichloride, chloroform, carbon tetrachloride, ethylidene dichloride, dichlorethylene, trichloroethylene, bromoform, tetrabromomethane, dibromoethylene, and iodoform.

Examples of the products which may be obtained from specific reactants are shown below.

| Hydrocarbon | Halocarbon | Product |
| --- | --- | --- |
| Methane | Methylene dichloride | Methyl chloride |
| Methane | Chloroform | Methyl chloride |
|  |  | Methylene dichloride |
|  |  | Carbon tetrachloride |
| Methane | Carbon Tetrachloride | Methyl chloride |
|  |  | Methylene dichloride |
|  |  | Chloroform |

-continued

| Hydrocarbon | Halocarbon | Product |
| --- | --- | --- |
| Ethane | (Ethylidene dichloride) (dichloroethane) | Ethyl Chloride |
| Ethane | Trichloroethylene | Dichloroethanes |

Catalyst

The hydrocarbon is halogenated with the halocarbon teactant in the presence of an acidic, crystalline aluminosilicate zeolite catalyst. Zeolites of this kind comprise a three dimensional lattice of $SiO_4$ tetrahedra crosslinked by the sharing of oxygen atoms and which may optionally contain other atoms in the lattice, especially aluminum in the form of $AlO_4$ tetrahedra; the zeolite will also include a sufficient cationic complement to balance the negative charge on the lattice. Zeolites have a porous crystal structure which is capable of regulating the access to an egress from the intracrystalline free space. This control, which is effected by the crystal structure itself, is dependent both upon the molecular configuration of the material which is or, alternatively, is not, to have access to the internal structure of the zeolite and also upon the structure of the zeolite itself. The pores of the zeolite are bounded by rings which are formed by the regular disposition of the tetrahedra making up the anionic framework of the crystalline aluminosilicate, the oxygen atoms themselves being bonded to the silicon or aluminum atoms at the centers of the tetrahedra. A convenient measure of the extent to which a zeolite provides this control for molecules of varying sizes to its internal structure is provided by the Constraint Index of the zeolite: zeolites which provide but highly restricted access to and egress from the internal structure have a high value for the Constraint Index and zeolites of this kind usually have pores of small size. Contrariwise, zeolites which provide relatively free access to the internal zeolite structure have a low value for the Constraint Index. The method by which Constraint Index is determined is described fully in U.S. Pat. No. 4,016,218 and J. Catalysis 67, 218–222 (1981) to which reference is made for details of the method together with examples of Constraint Index for some typical zeolites. Because Constraint Index is related to the crystalline structure of the zeolite but is nevertheless determined by means of a test which exploits the capacity of the zeolite to engage in a cracking reaction, that is, a reaction dependent upon the possession of acidic sites and functionality in the zeolite, the sample of zeolite used in the test should be representative of zeolitic structure whose Constraint Index is to be determined and should also possess requisite acidic functionality for the test. Acidic functionality may, of course, be varied by conventional artifices including base exchange, steaming or control of silica:alumina ratio.

A wide variety of acidic zeolites may be used in the present process including large pore zeolites such as faujasite, mordenite, zeolite X, zeolite Y and zeolite beta and small pore zeolites such as zeolite A but the most preferred group of zeolites are those which are characterized by a Constraint Index from 1 to 12 and a silica:alumina ratio of at least 12:1. These zeolites, the so-called intermediate pore size zeolites, are preferred because their pores are sufficiently large to permit ready access to their internal pore structure by simple hydrocarbons but, at the same time, are sufficiently small to preclude access by bulky coke precursors which otherwise would tend to enter the intracrystalline pore space of the zeolite and form coke which would eventually degrade the catalytic activity of the zeolite. This class of zeolites therefore offers the possibility of extended operation without the need for regeneration by removal of any coke which might be formed.

The silica:alumina ratios referred to in this specification are the structural or framework ratios, that is, the ratio for the $SiO_4$ to the $AlO_4$ tetrahedra which together constitute the structure of which the zeolite is composed. This ratio may vary from the silica:alumina ratio determined by various physical and chemical methods. For example, a gross chemical analysis may include aluminum which is present in the form of cations associated with the acidic sites on the zeolite, thereby giving a low silica:alumina ratio. Similarly, if the ratio is determined by thermogravimetric analysis (TGA) of ammonia desorption, a low ammonia titration may be obtained if cationic aluminum prevents exchange of the ammonium ions onto the acidic sites. These disparities are particularly troublesome when certain treatments such as dealuminization methods which result in the presence of ionic aluminum free of the zeolite structure are employed. Due care should therefore be taken to ensure that the framework silica:alumina ratio is correctly determined.

Specific zeolites conforming to the prescribed values of Constraint Index and silica:alumina ratio include ZSM-5, ZSM-11, ZSM-12, ZSM-23, ZSM-35, ZSM-38, the ZSM-5/ZSM-11 intermediate and ZSM-48 which are disclosed, respectively, in U.S. Pat. Nos. 3,702,886; 3,709,769; 3,832,449; 4,076,842; 4,016,245, 4,046,859 and 4,229,424 and European Patent Publication No. 15132. Highly siliceous forms of ZSM-5 are disclosed in U.S. Pat. No. Re. 29,948, of ZSM-11 in European Patent No. 14059 and of ZSM-12 in European Patent No. 13630. Reference is made to these patents for complete details of these zeolites and the preparation. Of them, ZSM-5 is preferred.

The silica:alumina ratio of the preferred catalysts is preferably at least 30:1 or even higher e.g. 70:1, 100:1, 300:1, 500:1 or even as high as 1600:1. Thus, the most preferred catalyst will be ZSM-5 with a silica:alumina ratio of 70:1 or higher.

Zeolite beta is disclosed in U.S. Pat. No. 3,308,069 to which reference is made for details of this zeolite and its preparation.

When the zeolites have been prepared in the presence of organic cations, they are catalytically inactive, possibly because the intracrystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of the zeolite; but it does appear to favor the formation of this special type of zeolite.

When synthesized in the alkali metal form, the zeolite is conveniently converted to the hydrogen form, generally by intermediate formation of the ammonium form as a result of ammonium ion exchange and calcination of the ammonium form to yield the hydrogen form.

It may be desirable to incorporate the zeolite in another material resistant to the temperature and other conditions employed in the process. Such matrix materials be synthetic or naturally occurring materials or in the form of gelatinous precipitates or gels including mixtures of silica and metal oxides. Naturally occurring clays can be composited with the zeolite and they may be used in the raw state as originally mined or initially subjected to calcination, acid treatment or chemical modification. Alternatively, the zeolite may be composited with a porous oxide matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia or silica-magnesia-zirconia. The matrix may be in the form of a cogel. The relative proportions of zeolite component and inorganic oxide gel matrix may vary widely with the zeolite content typically ranging from 1 to 99 percent by weight and more usually in the range of 5 to 80 percent weight of the composite.

Because the halogenation reaction is acid catalyzed, the zeolite should be at least partly in the hydrogen or acidic form. The acidity of the zeolite may conveniently be measured by its alpha value which is a measure of the relative activity of the zeolite with respect to a high activity silica:alumina cracking catalyst. A method for the determination of alpha is given in U.S. Pat. No. 4,016,218 and the Journal of Catalysis, Vol. VI, pages 278-287, 1966, to which reference is made for details of the method. The alpha value of the zeolite used in the present process will usually be at least 1 and, as a general rule, at least 10. The alpha values of the preferred HZSM-5 zeolites having a silica:alumina ratio of 70:1 are normally in the range of 10 to 50. Higher alpha catalysts may however be used. Alpha values may be varied by a number of known techniques such as steaming or sodium exchange, both of which reduce alpha. Alpha may be increased almost up to the theoretical limit set by the acid site density of the zeolite by ammonium exchange followed by calcination. The acidity of the zeolite may also be varied by control of the silica:alumina ratio of the zeolite, as described in U.S. Pat. No. 4,218,573, to which reference is made.

If the hydrocarbon reactant is incapable of being sorbed by the zeolites of the preferred class it may be necessary to use a larger pore zeolite such as faujasite, mordenite, zeolite X, zeolite Y or zeolite beta since zeolites of this class (which generally have a Constraint Index of less than 1) permit quite large molecules to enter and leave their pore structures so that catalysis of the desired reactions may take place. Use of these zeolites therefore offers the possibility of halogenating bulky hydrocarbons such as 2,2-dimethyl propane and other materials which are too large in terms of molecular size or have a steric configuration which otherwise precludes their access to the catalytic sites in the preferred types of zeolite.

Reaction Conditions

The reactants are passed over the zeolite catalyst under conditions of elevated temperature, usually at least 200° C. and, in most cases in the range of 200° to 650° C., preferably 300° to 550° C. The pressure is not critical and will normally range from atmospheric to much higher values, the maximum normally being dictated by practical considerations. Pressures from atmospheric up to 25,000 kPa are suitable, generally from atmospheric to 8000 kPa. Space velocities of the hydrocarbon reactant will normally be in the range of 0.1 to 20, preferably 0.1 to 10. The ratio of hydrocarbon reactant to the halocarbon reactant will be dictated to a certain extent by the stoichiometry of the reaction required to produce the desired products but will normally employ an excess of the hydrocarbon reactant if an excessive degree of halogenation is to be avoided. On the other hand, if highly halogenated products are desired, an excess of the halocarbon reactant may become necessary.

With simple hydrocarbon substrates, especially methane, the reaction proceeds with good selectivity to the products desired, thereby reducing the need for the complicated and expensive separations which accompanied halogenation processes using the halogen itself as the halogenating agent. However, if desired, fractionation or separation by other physical or chemical means may be used in order to obtain the desired product in the requisite state of purity.

The invention is illustrated by the following example in which all parts, proportions and percentages are by weight.

EXAMPLE

Methane and chloroform were passed over HZSM-5 (70:1 silica:alumina ratio) at 400° C., atmospheric pressure to yield the following products:

|  | Percent |
| --- | --- |
| Methyl chloride | 73 |
| Dichloromethane | 6 |
| Carbon tetrachloride | 21 |
| Dichloroethylene | tr. |
| Trichloroethylene | tr. |
| Tetrachloroethylene | tr. |

For comparison, the chloroform was passed over the HZSM-5 catalyst under the same conditions but with the methane replaced by nitrogen. The only carbon-containing product was carbon tetrachloride.

For further comparison, when the same mixture of methane and chloroform were passed over quartz chips ("Vycor"—trademark) instead of HZSM-5, only trace amounts of dichloromethane and carbon tetrachloride were detected; no methyl chloride was produced.

We claim:

1. A process for producing halocarbons which comprises passing a halogen acceptor and a halocarbon reactant over an acidic, crystalline aluminosilicate zeolite catalyst having a constraint index of 1 to 12 and a silica:alumina ratio of at least 12:1 to form a halogenated product by halogenation of the halogen acceptor.

2. A process according to claim 1 in which the halocarbon reactant is a polyhalocarbon.

3. A process according to claim 2 in which the polyhalocarbon is chloroform or carbon tetrachloride.

4. A process according to claim 1 in which the halogen acceptor is a hydrocarbon.

5. A process according to claim 4 in which the hydrocarbon comprises a straight chain lower alkane.

6. A process according to claim 5 in which the alkane is methane.

7. A process according to claim 6 in which methane is passed over the zeolite catalyst with chloroform as the halocarbon reactant.

8. A process according to claim 1 in which the zeolite has a silica:alumina ratio of at least 70:1.

9. A process according to claim 1 in which the zeolite is ZSM-5.

10. A process for producing halocarbons from a hydrocarbon, which comprises passing the hydrocarbon over an acidic, crystalline aluminosilicate zeolite catalyst comprising a crystalline aluminosilicate zeolite having a constraint index of 1 to 12 and a silica:alumina ratio of at least 12 to 1 in the presence of a halocarbon to halogenate the hydrocarbon.

11. A process according to claim 10 in which the hydrocarbon is a straight chain lower alkane.

12. A process according to claim 11 in which the alkane is methane.

13. A process according to claim 11 in which the halocarbon is a polyhalocarbon.

14. A process according to claim 13 in which the halocarbon is chloroform.

15. A process according to claim 10 in which the zeolite is ZSM-5.

16. A process according to claim 10 in which the zeolite is ZSM-5 having a silica:alumina ratio of at least 70:1.

17. A process according to claim 10 in which the hydrocarbon is methane, the halocarbon is a polyhalocarbon and the zeolite is ZSM-5.

18. A process for producing halocarbons from a hydrocarbon over an acidic crystalline aluminosilicate zeolite catalyst in the presence of a halocarbon to halogenate the hydrocarbon.

19. Process of claim 18 in which the hydrocarbon is a straight chain lower alkane.

20. Process of claim 19 in which the alkane is methane.

21. Process of claim 18 in which the halocarbon is a polyhalocarbon.

22. Process of claim 21 in which the halocarbon is chloroform.

23. Process of claim 18 in which the zeolite catalyst comprises a crystalline aluminosilicate zeolite having a Constraint Index of 1 to 12 and a silica:alumina ratio of at least 12:1.

24. Process of claim 23 in which the zeolite is ZSM-5.

25. Process of claim 24 in which the zeolite is ZSM-5 having a silica:alumina ratio of at least 70:1.

* * * * *

UNITED STATES PATENT AND TRADEMARK OFFICE
CERTIFICATE OF CORRECTION

PATENT NO. : 4,654,449

DATED : March 31, 1987

INVENTOR(S) : Clarence D. Chang et al

It is certified that error appears in the above-identified patent and that said Letters Patent is hereby corrected as shown below:

Column 3, line 48 delete "(Freon-22)" and insert --(Freon-12)--.

Column 4, line 11 delete "teactant" and insert --reactant--.

Column 8, Claim 16, delete "10" and insert --13--.

Signed and Sealed this

Twenty-ninth Day of December, 1987

*Attest:*

DONALD J. QUIGG

*Attesting Officer*   Commissioner of Patents and Trademarks